US008275141B2

(12) United States Patent
Pan et al.

(10) Patent No.: US 8,275,141 B2
(45) Date of Patent: Sep. 25, 2012

(54) NOISE REDUCTION SYSTEM AND NOISE REDUCTION METHOD

(75) Inventors: Shih-Yu Pan, Yongkang (TW); Min-Qiao Lu, Yongkang (TW); Jiun-Bin Huang, Taichung (TW); Shyang-Jye Chang, Xindian (TW)

(73) Assignee: Industrial Technology Research Institute, Hsinchu (TW)

( * ) Notice: Subject to any disclaimer, the term of this patent is extended or adjusted under 35 U.S.C. 154(b) by 189 days.

(21) Appl. No.: 12/771,024

(22) Filed: Apr. 30, 2010

(65) Prior Publication Data

US 2011/0103603 A1 May 5, 2011

(30) Foreign Application Priority Data

Nov. 3, 2009 (TW) .............................. 98137334 A

(51) Int. Cl.
*A61F 11/06* (2006.01)

(52) U.S. Cl. ................. 381/71.1; 381/71.11; 381/71.12; 381/92; 704/226; 704/E21.004

(58) Field of Classification Search ...... 381/71.1–71.14, 381/94.1–94.9, 92; 704/224–228, E21.001–E21.006
See application file for complete search history.

(56) References Cited

U.S. PATENT DOCUMENTS 5,471,538 A * 11/1995 Sasaki et al. .................... 381/92
5,754,665 A 5/1998 Hosoi
5,917,921 A 6/1999 Sasaki et al.
6,888,949 B1 5/2005 Vanden Berghe et al.
6,937,978 B2 * 8/2005 Liu .............................. 704/228
7,092,529 B2 * 8/2006 Yu et al. ..................... 381/71.11
7,174,022 B1 * 2/2007 Zhang et al. .................... 381/92
7,181,026 B2 * 2/2007 Zhang et al. .................... 381/92
7,248,708 B2 7/2007 Vaudrey et al.
7,330,556 B2 2/2008 Kates
7,386,135 B2 * 6/2008 Fan ................................ 381/92
8,068,619 B2 * 11/2011 Zhang et al. .................... 381/92
2009/0111507 A1 * 4/2009 Chen .......................... 455/550.1

* cited by examiner

*Primary Examiner* — Vivian Chin
*Assistant Examiner* — Fatimat O Olaniran
(74) *Attorney, Agent, or Firm* — Thomas|Kayden

(57) ABSTRACT

A noise reduction system and a noise reduction method are provided. The noise reduction system comprises a uni-directional microphone, an omni-directional microphone and a signal processing module. The signal processing module comprises an adaptive noise control (ANC) unit, a main noise reduction unit and an optimizing unit. The uni-directional microphone senses a first audio source to output a first audio signal, and the omni-directional microphone senses a second audio source to output a second audio signal. The ANC unit executes an adaptive noise control to output an estimated signal according to the first audio signal and the second audio signal. The main noise reduction unit executes a main noise reduction process to output a de-noise speech signal according to the estimated signal and the second audio signal. The optimizing unit executes an optimizing process to output an optimized speech signal according to the de-noise speech signal.

20 Claims, 5 Drawing Sheets

NOISE REDUCTION SYSTEM AND NOISE REDUCTION METHOD

This application claims the benefit of Taiwan application Serial No. 98137334, filed Nov. 3, 2009, the subject matter of which is incorporated herein by reference.

BACKGROUND OF THE DISCLOSURE

1. Technical Field

The disclosure relates in general to a noise reduction system and the noise reduction method, and more particularly to a noise reduction system and a noise reduction method capable of improving the communication quality.

2. Description of the Related Art

A mobile communication device is getting more and more important to modern people. In the trains, subways, stations or downtown, when people communicate with others, the audio quality of their mobile phones or PDAs is crucial. Especially, noises are everywhere nowadays, largely affecting people's everyday life and interfering with the communication quality.

Noise is present everywhere, affects human daily life and disturbs the communication between speakers and listeners. The background noise and the speaker's voice will be mixed together and received by the microphone of the mobile communication device when a mobile communication device is used. Environment or background noise can contaminate the speech signal; affect the communication quality or even harsh to the listener's ear. Therefore, it will be an imminent issue to avoid the surrounding background noise affecting the communication and to provide the best quality of speech.

SUMMARY

The disclosure is directed to a noise reduction system and a noise reduction method.

According to the first aspect of the present disclosure, a noise reduction system is provided. The noise reduction system comprises a uni-directional microphone, an omni-directional microphone and a signal processing module. The signal processing module comprises an adaptive noise control (ANC) unit, a main noise reduction unit and an optimizing unit. The uni-directional microphone senses a first audio source to output a first audio signal, and the omni-directional microphone senses a second audio source to output a second audio signal. The ANC unit executes an adaptive noise control to output an estimated signal according to the first audio signal and the second audio signal. The main noise reduction unit executes a main noise reduction process to output a de-noise speech signal according to the estimated signal and the second audio signal. The optimizing unit executes an optimizing process to output an optimized speech signal according to the de-noise speech signal.

According to the second aspect of the present disclosure, a noise reduction method is provided. The noise reduction method at least comprises the following steps. Firstly, a uni-directional microphone is provided for sensing a first audio source to output a first audio signal, and an omni-directional microphone is provided for sensing a second audio source to output a second audio signal. Next, an adaptive noise control (ANC) is executed to output an estimated signal according to the first audio signal and the second audio signal. Then, a main noise reduction process is executed to output a de-noise speech signal according to the estimated signal and the second audio signal. Lastly, an optimizing process is executed to output an optimized speech signal according to the de-noise speech signal.

The disclosure will become apparent from the following detailed description of the preferred but non-limiting embodiments. The following description is made with reference to the accompanying drawings.

DETAILED DESCRIPTION

A noise reduction system and a noise reduction method are disclosed in the embodiments below. The noise reduction system comprises a uni-directional microphone, an omni-directional microphone and a signal processing module. The signal processing module comprises an adaptive noise control (ANC) unit, a main noise reduction unit and an optimizing unit. The uni-directional microphone senses a first audio source to output a first audio signal, and the omni-directional microphone senses a second audio source to output a second audio signal. The ANC unit executes an adaptive noise control to output an estimated signal according to the first audio signal and the second audio signal. The main noise reduction unit executes a main noise reduction process to output a de-noise speech signal according to the estimated signal and the second audio signal. The optimizing unit executes an optimizing process to output an optimized speech signal according to the de-noise speech signal.

The noise reduction system at least comprises the following steps. Firstly, a uni-directional microphone is provided for sensing a first audio source to output a first audio signal, and an omni-directional microphone is provided for sensing a second audio source to output a second audio signal. Next, an adaptive noise control (ANC) is executed to output an estimated signal according to the first audio signal and the second audio signal. Then, a main noise reduction process is executed to output a de-noise speech signal according to the estimated signal and the second audio signal. Lastly, an optimizing process is executed to output an optimized speech signal according to the de-noise speech signal.

Figure 1:
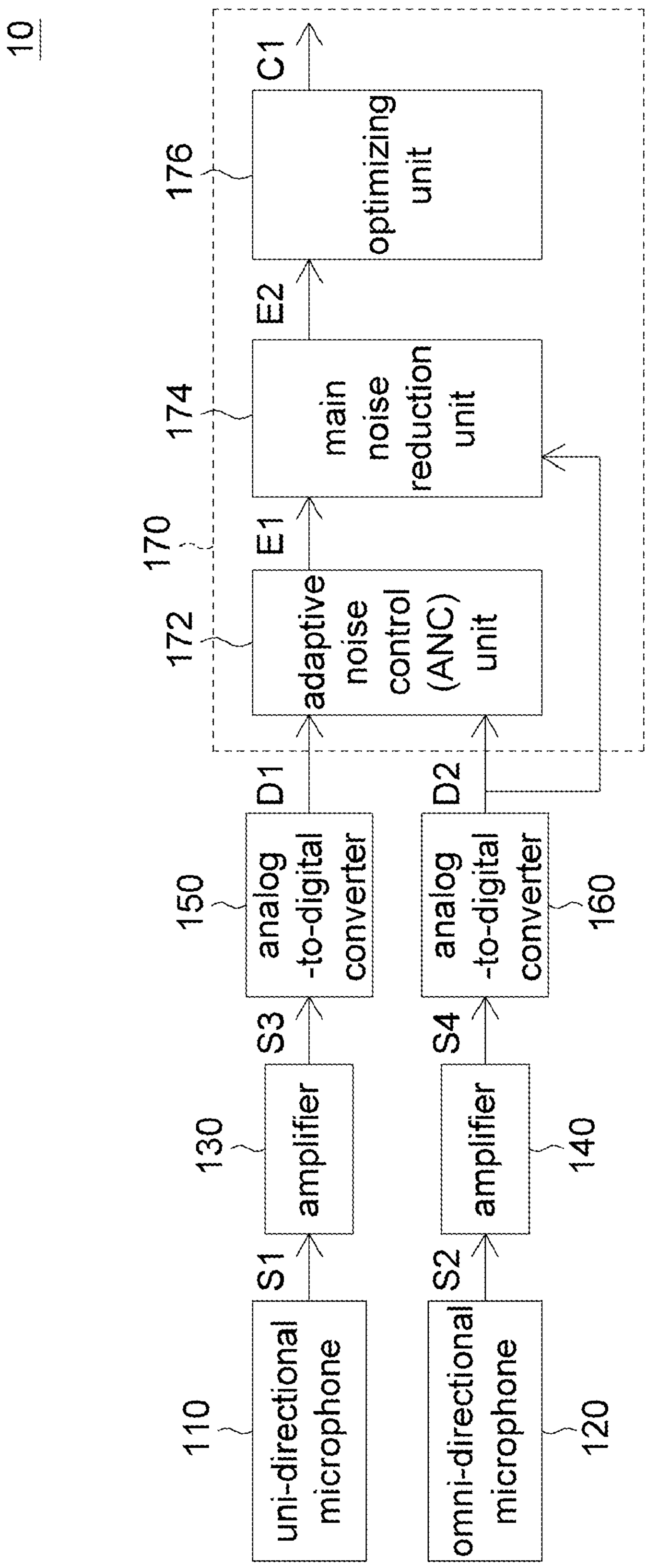
FIG. 1 is a block diagram of a noise reduction system according to the first exemplary embodiment.
Figure 2:
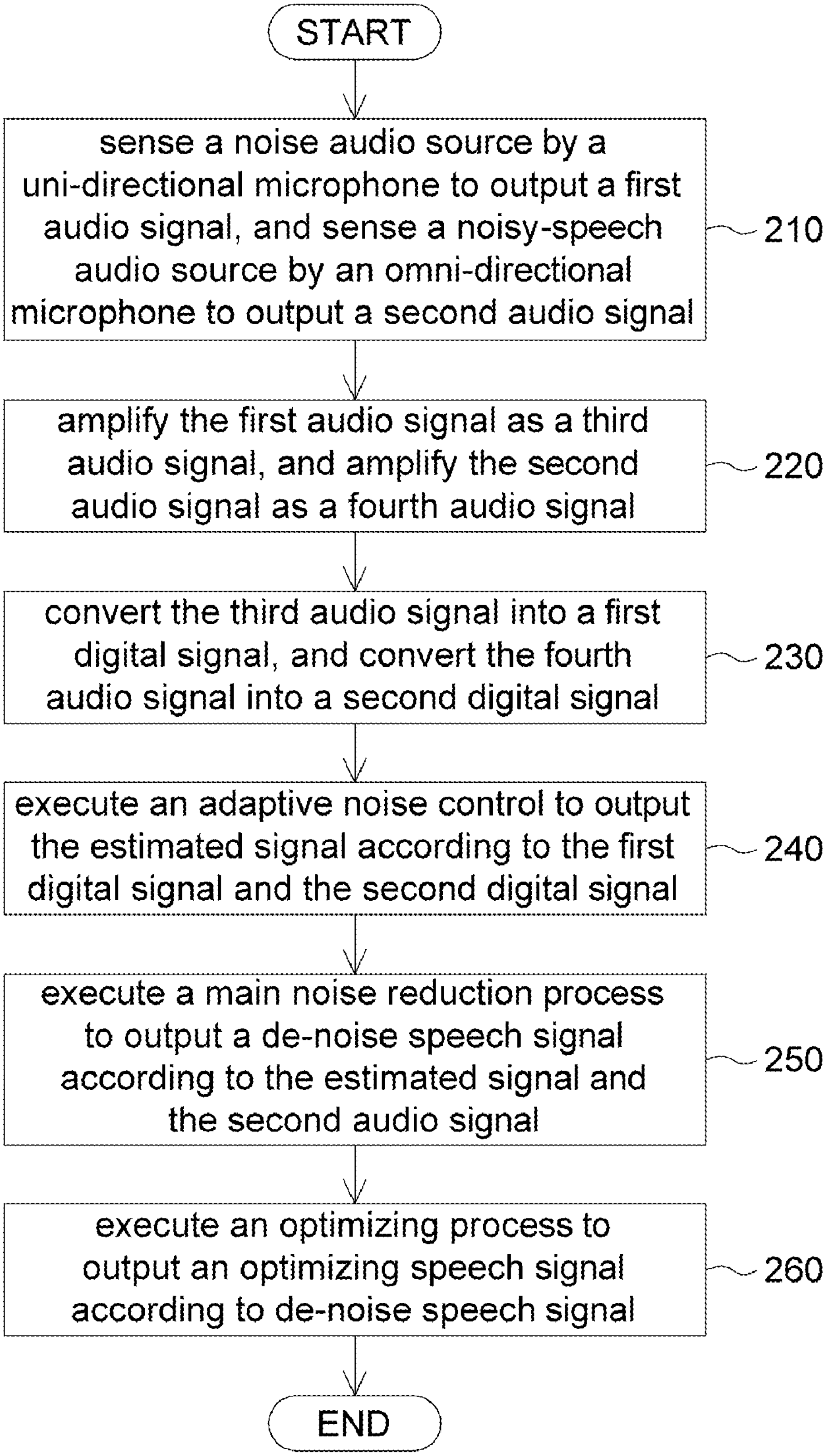
FIG. 2 is a flowchart of a noise reduction method according to the first exemplary embodiment.

Referring to FIG. 1 and FIG. 2, FIG. 1 is a block diagram of a noise reduction system according to the first embodiment. FIG. 2 is a flowchart of a noise reduction method according to the first embodiment. The noise reduction system 10 comprises a uni-directional microphone 110, an omni-directional microphone 120, two amplifiers 130 and 140, two analog-to-digital converters 150 and 160 and a signal processing module 170. The signal processing module 170 comprises an adaptive noise control (ANC) unit 172, a main noise reduction unit 174 and an optimizing unit 176.

The noise reduction method of the disclosure can be adapted in the noise reduction system 10. The noise reduction method at least comprises the following steps. Firstly, as indicated in step 210, the noise reduction system 10 senses a noise audio source by a uni-directional microphone 110 to output a first audio signal S1, and the noise reduction system 10 senses a noisy-speech audio source by an omni-directional microphone 120 to output a second audio signal S2. For the convenience of elaboration, in one embodiment, the uni-directional microphone 110 senses a noise audio source and the omni-directional microphone 120 senses a noisy-speech audio source, but in another embodiment, the uni-directional microphone 110 senses a speech audio source to output the first audio signal S1, and the omni-directional microphone 120 senses a noisy-speech audio source to output the second audio signal S2. The uni-directional microphone 110 and the omni-directional microphone 120 are such as the micro-electro mechanical systems (MEMS) microphone or the electret condenser microphone (ECM). As the noise reduction system 10 senses a noise audio source by the uni-directional microphone 110, the first audio signal S1 is much similar to noise.

Next, as indicated in step 220, the amplifier 130 amplifies the first audio signal S1 as a third audio signal S3, and the second amplifier 140 amplifies the second audio signal S2 as a fourth audio signal S4. Then, as indicated in step 230, the analog-to-digital converter 150 converts the third audio signal S3 into a first digital signal D1 which is outputted to the ANC unit 172, and the analog-to-digital converter 160 converts the fourth audio signal S4 into a second digital signal D2 which is outputted to the ANC unit 172.

Afterwards, as indicated in step 240, the ANC unit 172 executes an adaptive noise control to output an estimated signal E1 according to the first digital signal D1 and the second digital signal D2. The estimated signal E1 is such as an estimated noise or an estimated speech. As the first audio signal S1 is much similar to noise, the ANC unit 172 filters the speech component off the first digital signal D1 to obtain a purer estimated noise according to the second digital signal D2. Likewise, as the first audio signal S1 is similar to speech, the ANC unit 172 filters the noise component off the second digital signal D2 to obtain a purer estimated speech according to the first digital signal D1. Examples of the foregoing adaptive noise control include the least mean square (LMS) algorithm and normalized least mean square (NLMS) algorithm.

After that, as indicated in step 250, the main noise reduction unit 174 executes a main noise reduction process to output a de-noise speech signal E2 according to the estimated signal E1 and the second digital signal D2. Examples of the main noise reduction process include the Wiener filter, the adaptive noise control, the subspace method and the Kalman filter.

Lastly, as indicated in step 260, the optimizing unit 176 executes an optimizing process to output an optimized speech signal C1 according to the de-noise speech signal E2. The optimizing unit 176 reduces the noise that cannot be reduced by the main noise reduction unit 174 or enhances the volume of the de-noise speech signal E2. Examples of the optimizing process include the high pass filter, the low pass filter, the band pass filter and the band stop filter.

All of the methods or algorithms mentioned in this disclose, including the adaptive noise control, the main noise reduction process, and the optimizing process, perform the signal processing in the time domain. That is, no signal processing in the frequency domain is required.

Figure 3:
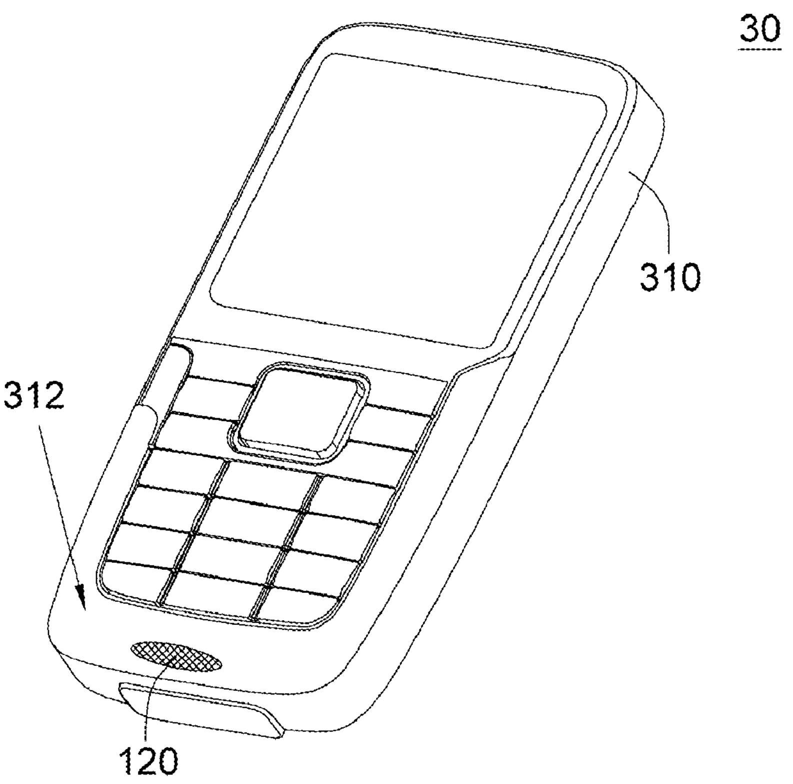
FIG. 3 and FIG. 4 respectively are perspective views at different angles of the first type mobile communication device.
Figure 4:
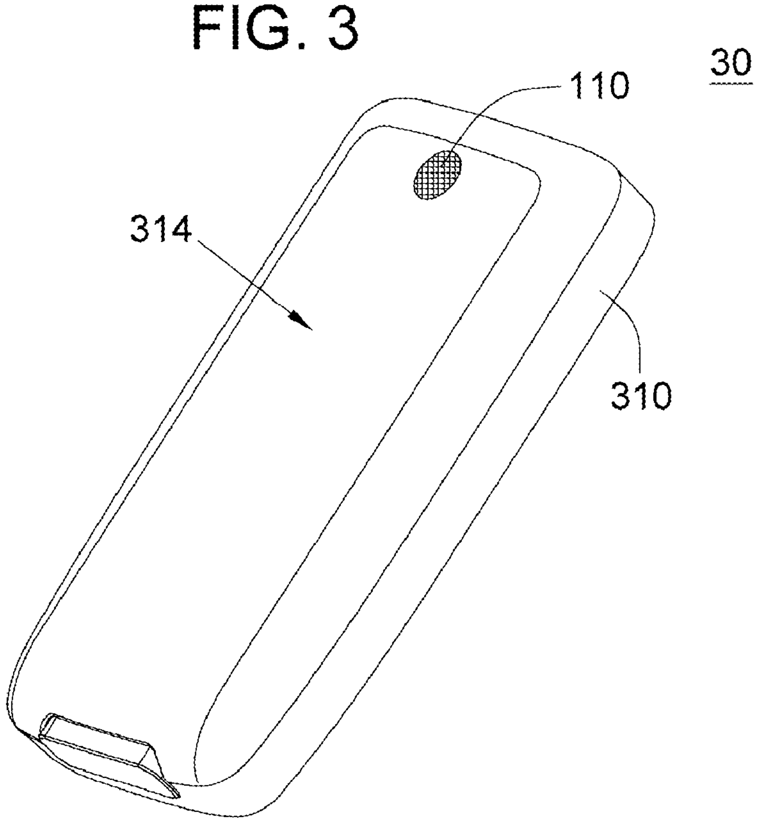

Referring to FIG. 3 and FIG. 4, FIG. 3 and FIG. 4 are respectively perspective views at different angles of the first type mobile communication device. The noise reduction system 10 of FIG. 1 can be adapted in a mobile communication device 30, such as bar type mobile phone or slide type mobile phone. The mobile communication device 30 comprises a housing 310 comprising a reception plane 312 and a non-reception plane 314. When the user answers or makes a call with the mobile communication device 30, the reception plane 312 is close to the user's mouth, and the non-reception plane 314 can be any plane on the housing 310 other than the reception plane 312. In FIG. 3 and FIG. 4, for example, the non-reception plane 314 and the reception plane 312 are opposite to each other. When the user uses the mobile phone to communicate with others, the omni-directional microphone 120 disposed on the reception plane 312 senses the generated noisy-speech audio source and the uni-directional microphone 110 disposed on the non-reception plane 314 senses the background noise source. Because the uni-directional microphone 110 is sensitive to the sound within some directed range, the uni-directional microphone 110 disposed on the non-reception plane 314 makes the first audio signal S1 be much similar to the surrounding noise. Then, the ANC unit 172 of FIG. 1 can separate the estimated noise component from the second audio signal S2 based on that the first audio signal S1 is similar to the noise source. Furthermore, the ANC unit 172 can separate the estimated speech component from the second audio signal S2 if the noise is known.

Figure 5:
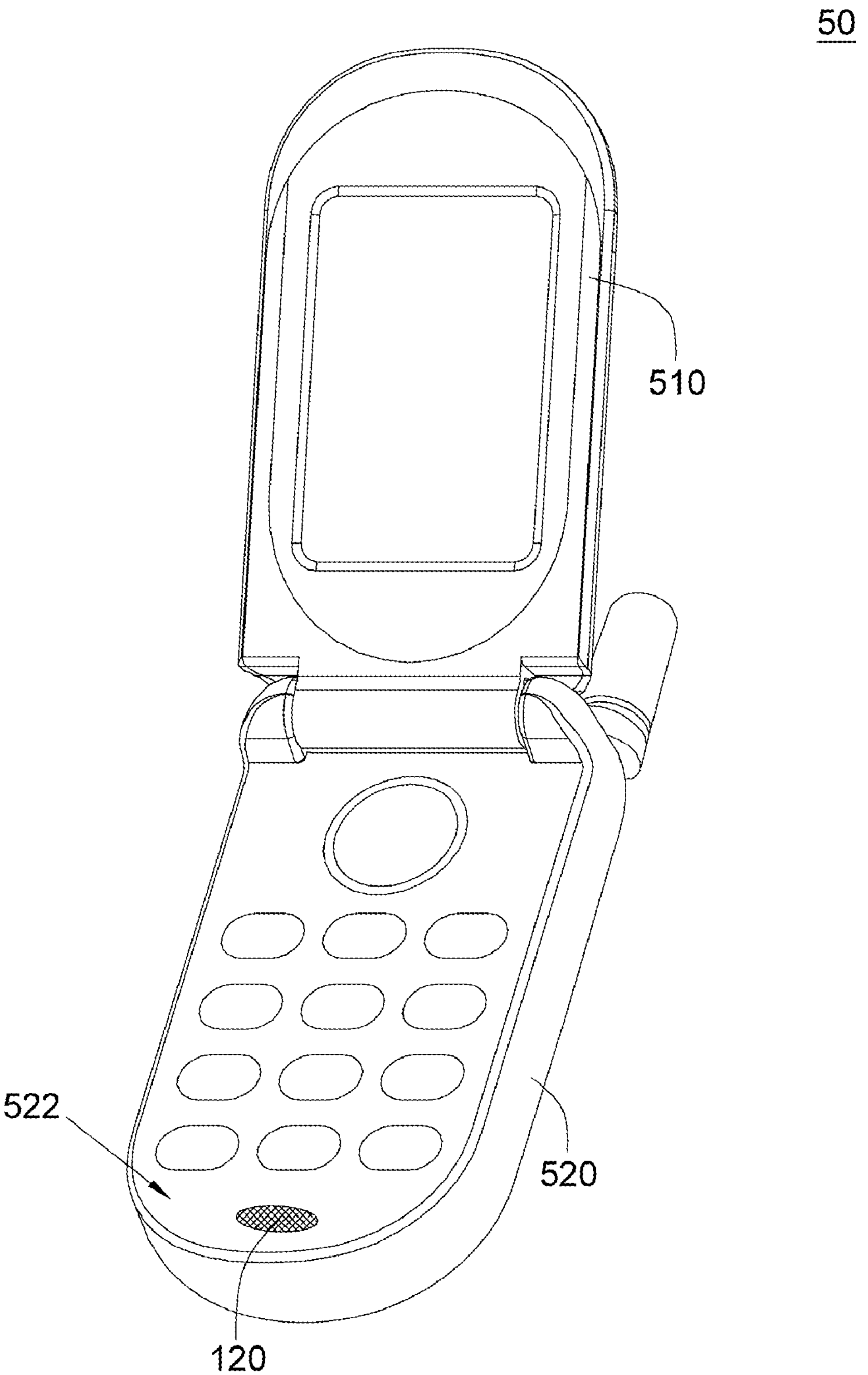
FIG. 5 and FIG. 6 respectively are perspective views at different angles of the second type mobile communication device.
Figure 6:
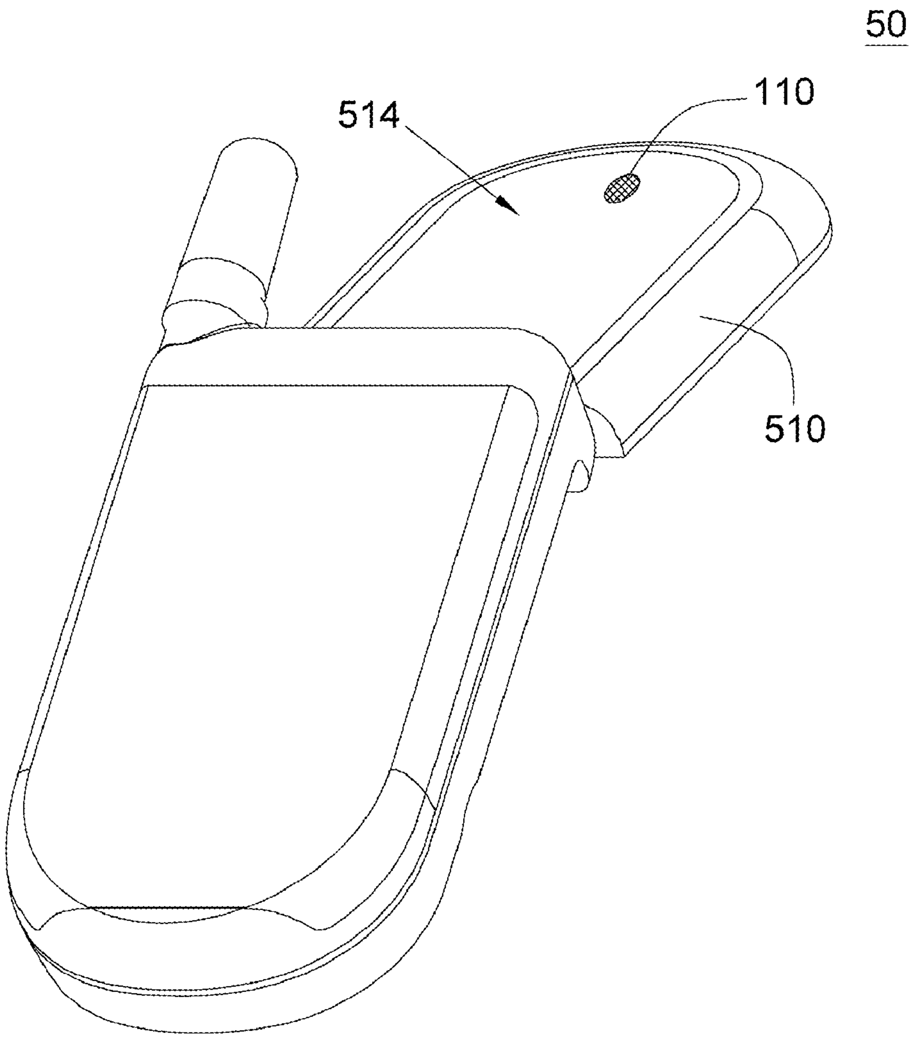

Referring to FIG. 5 and FIG. 6, FIG. 5 and FIG. 6 are respectively perspective views at different angles of the second type mobile communication device. The noise reduction system 10 of FIG. 1 can be adapted in a mobile communication device 50, such as a flip top mobile phone. The mobile communication device 50 comprises an upper cover 510 and a lower cover 520. The upper cover 510 comprises a non-reception plane 514 and a lower cover 520 which comprises a reception plane 522. When the user answers or makes a call with the mobile communication device 50, the upper cover 510 is flipped from the lower cover 520. After the upper cover 510 is flipped, the reception plane 522, i.e. the plane on the lower cover 520, is close to the user's mouth, and the non-reception plane 514 can be any plane other than the reception plane 522. When the user utilizes the mobile phone to talk to others, the omni-directional microphone 120 disposed on the reception plane 522 senses the generated noisy-speech audio source and the uni-directional microphone 110 disposed on non-reception plane 514 senses the surrounding noise source. Because the uni-directional microphone 110 is sensitive to the sound within some directed range, the uni-directional microphone 110 disposed on the non-reception plane 514 makes the first audio signal S1 be much similar to the surrounding noise source. Based on the above viewpoint, the ANC unit 172 of FIG. 1 can separate the estimated noise component from the second audio signal S2. Furthermore, the ANC unit 172 can separate the estimated speech component from the second audio signal S2 if the noise is known.

Figure 7:
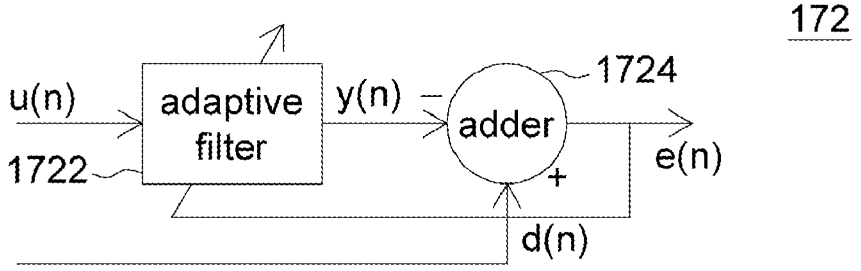
FIG. 7 is a schematic diagram illustrating an ANC unit.

Referring to FIG. 7, an ANC unit is shown. The ANC unit 172 comprises an adaptive filter 1722 and an adder 1724. In the ANC unit 172, the estimated signal E1 is regarded as an estimated noise or estimated speech, and the first digital signal D1 or the second digital signal D2 of FIG. 1 is selected as a desired value d(n). If the second digital signal D2 is a desired value d(n), the first digital signal D1 is an input vector u(n). In other words, if the first digital signal D1 is a desired value d(n), the second digital signal D2 is an input vector u(n). For example, in the ANC unit 172, in order to make the estimated signal E1 be an estimated noise, the first digital signal D1 is selected as a desired value d(n) and the second digital signal D2 is selected as an input vector u(n). Also, as shown in the ANC unit 172 of FIG. 7, the output data y(n) in FIG. 7 is the estimated signal E1 of FIG. 1 and is similar to the noise.

Examples of the adaptive noise control algorithm executed by the ANC unit 172 include the least mean square (LMS)

algorithm and normalized least mean square (NLMS) algorithm. The well-known feature of the least mean square algorithm, the most widely used filter algorithm, is simple. The least mean square algorithm uses the addition and multiplication instead of using the correlation function or matrix inversion.

The least mean square (LMS) algorithm is to use the method of steepest descent to find a weight coefficient vector, W, which minimizes a cost function, J(n), that is defined as $J(n)=e(n)^2$, n=0, 1, 2, . . . . The difference between the desired value d(n) and the estimated signal is called the "estimation error", e(n), and the error signal is defined as $e(n)=d(n)-W^T(n)u(n)$. Wherein, W(n) is a weight coefficient vector at the time point n, and is expanded as $W(n)=[w_0\ w_1 \ldots w_{L-1}]^T$. u(n) is an output vector, and is expanded as $u(n)=[u(n)\ u(n-1) \ldots u(n-L+1)]^T$. L denotes the filter order (or filter length). Therefore, the least mean square algorithm mainly adjusts the error value e(n) between the desired value d(n) of the noise reduction system 10 and the output data y(n) of the adaptive filter 1722. In the mean time, the least mean square algorithm keeps updating the weight coefficient vector W(n) value of the algorithm and makes the square of the error signal value e(n) be minimized. The calculation of the least mean square algorithm is disclosed below: the output data of the adaptive filter 1722 is expressed as: $y(n)=W^T(n-1)u(n)$. The adder 1724 generates an error value expressed as: $e(n)=d(n)-y(n)$ according to the output data y(n) and the desired value d(n). The weight coefficient vector at the next time point n+1 is expressed as: $W(n+1)=W(n)+\mu[u(n)e(n)]$.

The selection of the step-sized parameter μ value of the least mean square algorithm is very important. The μ value is used for adjusting the correction (training) speed of weighted parameters, W. If the selected μ value is too low, the convergence speed of the W value will slow down; if the selected μ value is too high, the convergence of the W value will be unstable and even become divergent. Therefore, the search of an optimum μ value is crucial to the least mean square algorithm. The selection of μ value is subject to certain restrictions with the convergence condition being expressed as:

$$0 < \mu < \sum_{k=0}^{L-1} E\{|u(n-k)^2|\}.$$

The normalized least mean square algorithm also adjusts and keeps updating the weight coefficient vector W(n) to make the square of the error signal value e(n) minimized. Furthermore, the normalized least mean square algorithm re-defines the μ value of the least mean square algorithm, so that the μ value changes along with the normalization of the input signal so as to improve the convergence stability. In the calculation of the normalized least mean square algorithm, the error value is expressed as: $e(n)=d(n)-y(n)$; the output data is expressed as: $y(n)=W^T(n-1)u(n)$; the weight coefficient vector is expressed as:

$$W(n+1) = W(n) + \frac{\mu e(n)u(n)}{\alpha + \|u(n)\|^2},$$

and the μ value is expressed as:

$$\mu(n) = \frac{\mu}{\|u(n)\|^2}.$$

The definitions of the parameters of the normalized least mean square algorithm are the same with that of the least mean square algorithm. To avoid the W being diverged if the input signal is too low, an α value is further added, wherein the added parameter is a small positive constant expressed as: α=1e−10.

The noise reduction system and the noise reduction method disclosed in the above embodiments of the disclosure filter off unnecessary background noise so as to provide the better speech quality. Moreover, the signal processing module performs the signal processing in the time domain instead of performing the signal processing in the frequency domain. The signal processing module not only can reduce noise effectively but also simplify the complicated calculation.

While the disclosure has been described by ways of examples and in terms of a preferred embodiment, it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A noise reduction system, comprising:

a uni-directional microphone for sensing a first audio source to output a first audio signal, wherein the first audio source is a speech audio source and the first audio signal is similar to speech;

an omni-directional microphone for sensing a second audio source to output a second audio signal, wherein the second audio source is a noisy-speech audio source; and a signal processing module, comprising:

an adaptive noise control (ANC) unit for executing an adaptive noise control to output an estimated signal according to the first audio signal and the second audio signal, wherein the estimated signal is an estimated speech purer than the first audio signal;

a noise reduction unit for executing a noise reduction process to output a de-noise speech signal according to the estimated signal and the second audio signal; and an optimizing unit for executing an optimizing process to output an optimized speech signal according to the de-noise speech signal.

2. The noise reduction system according to claim 1, wherein the noise reduction system is adapted in a mobile communication device, which comprises a housing comprising a reception plane where the omni-directional microphone is disposed on and a non-reception plane where the uni-directional microphone is disposed on, and the reception plane is opposite to the non-reception plane.

3. The noise reduction system according to claim 1, wherein the noise reduction system is adapted in a mobile communication device, which comprises an upper cover and a lower cover, the lower cover comprises a reception plane, the upper cover comprises a non-reception plane, the omni-directional microphone is disposed on the reception plane, and the uni-directional microphone is disposed on the non-reception plane.

4. The noise reduction system according to claim 1, wherein the adaptive noise control is the least mean square (LMS) or normalized least mean square (NLMS) algorithm.

5. The noise reduction system according to claim 1, wherein the noise reduction process is performed by a Wiener filter, a Kalman filter, or a subspace method.

6. The noise reduction system according to claim 1, wherein the optimizing unit not only reduces the noise that is not reduced by the noise reduction unit but also enhances the volume of the de-noise speech signal.

7. The noise reduction system according to claim 1, wherein the optimizing process is the high pass filter, low pass filter, band pass filter or band stop filter.

8. The noise reduction system according to claim 1, further comprising:

a first amplifier for amplifying the first audio signal as a third audio signal;

a second amplifier for amplifying the second audio signal as a fourth audio signal;

a first analog-to-digital converter for converting the third audio signal into a first digital signal which is outputted to the ANC unit; and a second analog-to-digital converter for converting the fourth audio signal into a second digital signal which is outputted to the ANC unit, wherein the ANC unit executes an adaptive noise control to output the estimated signal according to the first digital signal and the second digital signal.

9. The noise reduction system according to claim 8, wherein the noise reduction unit executes a noise reduction process to output the de-noise speech signal according to the estimated signal and the second digital signal.

10. A noise reduction method, comprising:

sensing a first audio source by a uni-directional microphone to output a first audio signal, and sensing a second audio source by an omni-directional microphone to output a second audio signal, wherein the first audio source is a speech audio source, the first audio signal is similar to speech and the second audio source is a noisy-speech audio source;

executing an adaptive noise control (ANC) to output an estimated signal according to a first audio signal and a second audio signal, wherein the estimated signal is an estimated speech purer than the first audio signal;

executing a noise reduction process to output a de-noise speech signal according to the estimated signal and the second audio signal; and executing an optimizing process to output an optimized speech signal according to the de-noise speech signal.

11. The noise reduction method according to claim 10, wherein the noise reduction method is adapted in a mobile communication device, which comprises a housing comprising a reception plane and a non-reception plane, the omni-directional microphone is disposed on the reception plane, and the uni-directional microphone is disposed on the non-reception plane, and the reception plane is opposite to the non-reception plane.

12. The noise reduction method according to claim 10, wherein the noise reduction method is adapted in a mobile communication device, which comprises an upper cover and a lower cover, the lower cover comprises a reception plane, the upper cover comprises a non-reception plane, the omni-directional microphone is disposed on the reception plane, and the uni-directional microphone is disposed on the non-reception plane.

13. The noise reduction method according to claim 10, wherein the adaptive noise control is the least mean square (LMS) or normalized least mean square (NLMS) algorithm.

14. The noise reduction method according to claim 10, wherein the noise reduction process is performed by a Wiener filter, a Kalman filter, or a subspace method.

15. The noise reduction method according to claim 10, wherein the optimizing unit not only can reduce the noise that cannot be reduced by the noise reduction unit but also can enhance the volume of the de-noise speech signal.

16. The noise reduction method according to claim 10, wherein the optimizing process is the high pass filter, low pass filter, band pass filter or band stop filter.

17. The noise reduction method according to claim 10, further comprising:

amplifying the first audio signal as a third audio signal, and amplifying the second audio signal as a fourth audio signal;

converting the third audio signal into a first digital signal, and converting the fourth audio signal into a second digital signal; and executing an adaptive noise control to output the estimated signal according to the first digital signal and the second digital signal.

18. The noise reduction method according to claim 8, wherein in the noise reduction process, a main noise reduction process is executed to output the de-noise speech signal according to the estimated signal and the second digital signal.

19. The noise reduction system according to claim 8, wherein the ANC unit filters a noise component off the second digital signal according to the first digital signal to obtain the estimated signal.

20. The noise reduction method according to claim 17, wherein the step of executing the adaptive noise control comprises filtering a noise component off the second digital signal according to the first digital signal to obtain the estimated signal.

* * * * *